US00PP13125P2

(12) United States Plant Patent
Heims

(10) Patent No.: US PP13,125 P2
(45) Date of Patent: Oct. 22, 2002

(54) CAMPANULA PLANT NAMED 'SNOWBALL'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,647

(22) Filed: Jun. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Campanula plant characterized by a compact, upright, well-branched habit, and double white flowers.

2 Drawing Sheets

BOTANICAL CLASSIFICATION

*Campanula trachelium.*

VARIETY DENOMINATION

'Snowball'.

The present invention relates to a new and distinct hybrid of *Campanula trachelium,* of the family Campanulaceae, which originated as a seedling from *Campanula trachelium* 'Bernice'.

The new variety has been reproduced only by asexual propagation (division and tissue culture). Each of the progeny exhibits identical characteristics to the original plant.

This plant is characterized by the following:

1. Fully double white flowers held above the leaves.
2. Stiff upright, well-branched habit of growth.
3. Dwarfer habit than species.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
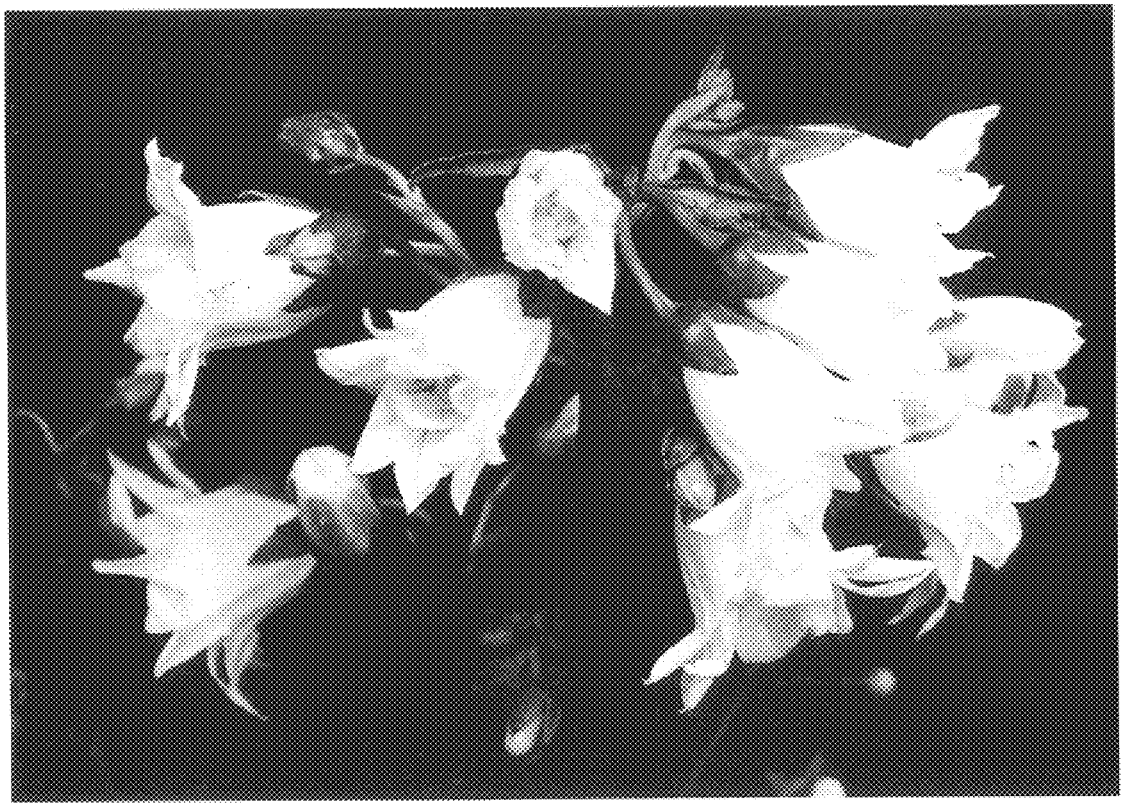
FIG. 1 shows Campanula 'Snowball' in flower.
Figure 2:
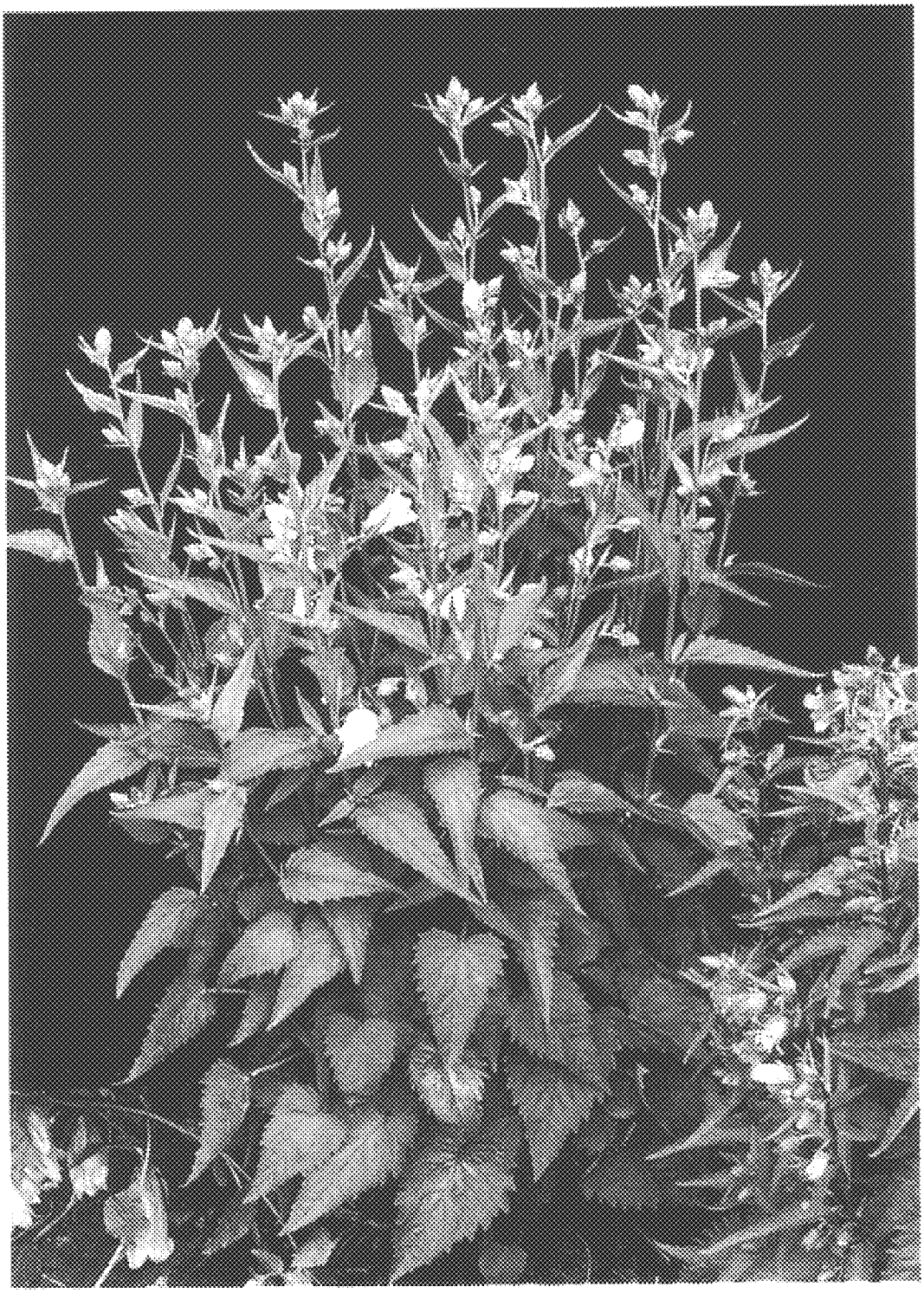
FIG. 2 shows the plant in the field in Canby, Oreg.

The following is a detailed description of the new Campanula hybrid based on observations of a one-and-a-half year old specimen grown in the trial field in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—30 cm. wide and 45 cm. tall.
- *Form.*—Basal clump.

Leaf:
- *Type.*—Simple.
- *Shape.*—Ovate-cordate.

- *Arrangement.*—Rosette.
- *Length.*—11.5 cm.
- *Width.*—8 cm. at the widest part.
- *Petiole length.*—Long, 14 to 19 cm.
- *Margins.*—Biserrate.
- *Apex.*—Acuminate.
- *Base.*—Cordate.
- *Leaf texture.*—Setose.
- *Petiole texture.*—Glabrous.
- *Petiole color.*—Yellow Green 146C.
- *Venation.*—Pinnate.
- *Color.*—Topside — Green 137A. Bottom — Closest to Yellow Green 147B.

Cauline leaves (found in the spring on the flowering stems):
- *Type.*—Simple.
- *Arrangement.*—Alternate.
- *Shape.*—Ovate lanceolate near bottom of the stem and lanceolate near the top.
- *Length.*—7 to 13.5 cm.
- *Width.*—2.3 to 4.7 cm.
- *Margins.*—Doubly serrate.
- *Apex.*—Acuminate.
- *Base.*—Truncate on lower leaves to obtuse on upper leaves.
- *Leaf texture.*—Setose.
- *Venation.*—Pinnate.
- *Color.*—Same as regular leaves.

Inflorescence:
- *Type.*—Terminal panicle.
- *Peduncle.*—Height: 66 cm. Diameter: 6 cm. at widest. Texture: Setose, winged. Color: Yellow Green 146C.
- *Pedicel.*—Length: Varies. Grows to 1.4 cm. Texture: Setose. Color: Yellow Green 145A.
- *Flower number.*—Approximately 25 per panicle.

Flower bud:
- *Size.*—2–5 to 3 cm. long and 1 cm. wide.
- *Shape.*—Ovoid.
- *Color.*—White 155D.

Flower:
- *Type.*—Actinomorphic.
- *Shape.*—Campanulate.
- *Size.*—3 cm. deep and 4.2 cm. wide.
- *Corolla.*—Three layers of complete corollas with 6–8 ovate lobes and a partial corolla. Petals reflex.
- *Texture.*—Sparsely pubsecent.
- *Color.*—White 155D.

*Calyx*.—5 fused sepals, rotate, lobes ovate lanceolate, parted ½ way to base, setose.
*Calyx size*.—1.2 cm deep and 2.8 cm wide.
*Calyx color*.—Green 137A.
*Pistil*.—2.3 cm. long, Yellow Green 154D to C.
*Stamen number*.—10.
*Pollen color*.—Yellow 8A.
*Bloom period*.—June to July in Canby, Oreg.
*Fragrance*.—None.

Fruit:
*Type*.—3-celled capsule.
*Color*.—Tan, Grey Brown 199D.

Seed:
*Color*.—Grey Brown 199A.
*Size*.—About 1 mm.
*Shape*.—Oval.
*Fertility*.—Fertile.

Disease: None observed on plant grown under commercial conditions in Canby, Oreg.

COMPARISONS TO SIMILAR CAMPANULA

Compared to *Campanula trachelium* 'Bernice', an unpatented plant, this new cultivated variety has white double flowers rather than blue.

Compared to *Campanula trachelium* 'Alba Flore Plena', this new cultivated variety is fully double rather than semi-double and is better branched.

I claim:

1. A new and distinct hybrid of Campanula substantially as shown and described, characterized by a well-branched habit and double white flowers.

* * * * *